United States Patent [19]

Helsley et al.

[11] 3,997,557

[45] Dec. 14, 1976

[54] SUBSTITUTED N-AMINOALKYLPYRROLES

[75] Inventors: Grover C. Helsley, Pottersville;
Richard C. Effland, Sommerville;
Larry Davis, Flemington, all of N.J.

[73] Assignee: American Hoechst Corporation,
Bridgewater, N.J.

[22] Filed: Apr. 23, 1974

[21] Appl. No.: 463,374

[52] U.S. Cl. ............ 260/326.12 R; 260/247.5 FP;
260/268 BC; 260/309.6; 260/326.14 R;
260/326.15; 260/326.27; 260/326.61;
260/326.62; 260/326.9; 260/590 C; 260/590
FA; 260/326.5 B; 424/248; 424/250;
424/273; 424/274

[51] Int. Cl.² ............ C07D 209/02; C07D 209/04

[58] Field of Search ..... 260/326.15, 326.9, 326.27,
260/326.5 B, 326.62, 326.61, 326.12 R,
326.14 R

[56] References Cited

UNITED STATES PATENTS 3,621,027  11/1971  Schoen et al. ............... 260/326.15
3,818,008  6/1974  Eberle et al. ............... 260/326.9

*Primary Examiner*—R. J. Gallagher
*Attorney, Agent, or Firm*—Curtis, Morris & Safford

[57] ABSTRACT

Substituted N-aminoalkylpyrroles of the formula:

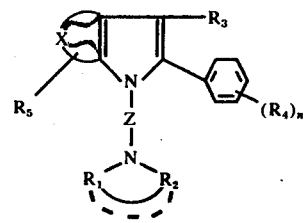

in which X, Z, $R_1$, $-R_5$ and n are as defined below, and their physiologically tolerable acid addition salts are disclosed to have antiarrhythmic, central nervous system depressant, antiinflammatory and antihypertensive activity. A process for their preparation is also disclosed.

14 Claims, No Drawings

SUBSTITUTED N-AMINOALKYLPYRROLES

This invention relates to substituted N-aminoalkylpyrroles having antiarrhythmic, central nervous system depressant, antiinflammatory, and analgesic activity, as well as to a process for the preparation thereof.

To the best of our knowledge, the compounds of this invention have not heretofore been described. 1-Aminoalkyl-2,6-diaryl-4,5,6,7-tetrahydroindoles are described in U.S. Pat. No. 3,621,027 and 6-aryl-4,5,6,7-tetrahydro-4-oxoindole derivatives are mentioned in U.S. Pat. No. 3,503,990. Antiestrogenic oxygen substituted 2-phenyl-4,5,6,7-tetrahydroindoles are mentioned in Deutsche Demokratische Republik Patentschrift No. 86826. However, the compounds of the present invention have marked structural differences and are prepared by different methods.

The compounds of the invention have the formula:

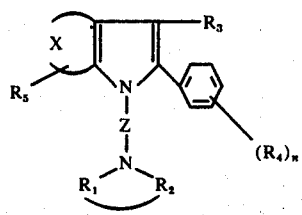

wherein Z represents a straight or branched, saturated or olefinically unsaturated hydrocarbon chain of 2-5 carbon atoms; $R_1$ represents a hydrogen atom or lower alkyl of from 1-3 carbon atoms; $R_2$ represents lower alkyl of from 1-3 carbon atoms or phenyl; or $R_1$ and $R_2$ together with the nitrogen atom to which they are attached form a heterocycle selected from the group consisting of pyrrolidinyl, piperidino, piperazinyl, imidazolidonyl, and morpholino; $R_3$ represents a hydrogen atom, phenyl or substituted phenyl; $R_4$ can be situated meta, ortho, or para and represents alkyl of from 1-6 carbon atoms, alkoxy of from 1-4 carbon atoms, halogen, trifluoromethyl, hydroxy, nitro, amino, cyano, acetamido, unsubstituted or substituted phenyl; n is the integer 0, 1, 2, or 3; and X is alkylene of from 3-7 carbon atoms,

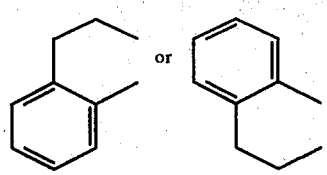

and $R_5$ is hydrogen, alkyl of from 1-5 carbon atoms, alkoxy of from 1-2 carbon atoms, or halogen; and their physiologically tolerable acid addition salts. The compounds of the present invention are useful as antiarrhythmic, central nervous system depressant, antiinflammatory, and antihypertensive agents.

The compounds of the present invention are prepared by condensation of an appropriate γ-diketone with an appropriate aminoalkylamine or aminoalkylenamine as illustrated in the following equation:

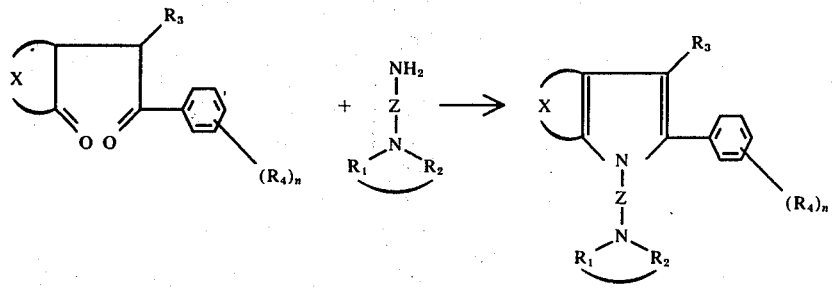

wherein X, Z, n, $R_1$, $R_2$ and $R_4$ are as defined earlier.

In the preferred procedure of the invention, the γ-diketone and the aminoalkylamine are allowed to react, with or without a solvent such as acetic acid or ethanol, at a temperature between 50°–120° C., for a period of time from several minutes to 24 hours in the presence or absence of an acidic catalyst such as hydrochloric acid.

When $R_4$ represents $NO_2$, the nitro can be reduced by methods known to the art such as by shaking a solution of the corresponding compound of the invention in glacial acetic acid on the Parr Hydrogenator with a Pd/C catalyst. Also, when $R_4$ represents Br, the bromo can be displaced with a cyano group by methods known to the art such as by reacting with cuprous cyanide.

The compounds of the invention are useful as antiarrhythmic agents because of their ability to alleviate cardiac arrhythmias. The activity of the compounds is demonstrated in the isolated rabbit atrium [B. Katzung in "Selected Pharmacological Testing Methods," Volume 3, edited by A. Berger, Marcel Dekker, New York (1968), p. 198] wherein the compounds effect an increase in the functional refractory period. Compounds are dissolved in Krebs-Henseleit solution, and the percent change in the functional refractory period is monitored with an oscilloscope. Thus, for example, at a concentration of $10^{-5}$ molar 1-(3-methylaminopropyl)-2-phenyl-1,4,5,6,7,8-hexahydrocyclohepta[b]pyrrole hydrochloride, 1-(2-diethylaminoethyl)-2-phenyl-5-methyl-4,5,6,7-tetrahydroindole hydrochloride, 1-(3-diethylaminopropyl)-2-phenyl-1,4,5,6,7,8-hexahydrocyclohepta[b]pyrrole hydrochloride, 1-(3-dimethylaminopropyl)-2-(p-nitrophenyl)-4,5,6,7,8,9-hexahydrocycloocta[b]pyrrole hydrochloride, 1-(3-dimethylaminopropyl)-2-(p-fluorophenyl)-4,5,6,7,8,9-hexahydrocycloocta[b]pyrrole oxalate, 1-(3-dimethylaminopropyl)-2-(p-methoxyphenyl)-4,5,6,7-tetrahydroindole hydrochloride and 1-(3-dimethylaminopropyl)-2-phenyl-1,4,5,6,7,8-hexahydrocyclohepta[b]pyrrole hydrochloride effect a 214%, 208%, 264%, 125% 139%, 300%, and 275% increase in the functional refractory period, respectively. Similarly at a concentration of $10^{-6}$ molar (1-(3-dimethylaminopropyl)-2-(p-bromophenyl)-4,5,6,7-tetrahydroindole hydrochloride and 1-(2-methylaminoethyl)-2-phenyl-1,4,5,6,7,8-hexahydrocyclohepta[b]pyrrole hydrochloride each effect a 150% increase in the functional refractory period. At a concentration of $2 \times 10^{-5}$ molar 1-(2-methylaminoethyl)-2-(m-trifluoromethylphenyl)4,5,6,7-tetrahydroindole hydrochloride, 1-(3-dimethylaminopropyl)-2-phenyl-1,4,5,6-tetrahydrocyclopenta[b]pyrrole hydrochloride and 1-(2-dimethylaminoethyl)-2-phenyl-4,5,6,7-tetrahydroindole hydrochloride effect a 200%, 233%, and 25% increase in the functional refractory period, respectively.

The compounds of the invention are useful as tranquilizers because of their depressant effects on the central nervous system. The depressant effects on the central nervous system were evaluated according to the mouse observation procedure of S. Irwin, Psychopharmacologia, 13, 222 (1968). Male COBS mice are dosed with the drug, and its effects on behavior and reflex depression together with muscle relaxation determined by the degree of deviation from control scores, with activity expressed in terms of minimum effective dose (MED). The effectiveness of compounds of the invention as tranquilizers is illustrated in Table I below.

Table I

| Compound | MED/Kilogram of body weight |
| --- | --- |
| 1-(3-dimethylaminopropyl)-2-(m-trifluoromethylphenyl)-4,5,6,7-tetrahydroindole | 40 mg |
| 1-(3-dimethylaminopropyl)-2-(p-methoxyphenyl)-4,5,6,7-tetrahydroindole . HCl | 50 mg |
| 1-(2-methylaminoethyl)-2-(m-trifluoromethylphenyl)-4,5,6,7-tetrahydroindole . HCl | 25 mg |
| 1-(3-dimethylaminopropyl)-2-phenyl-1,4,5,6-tetrahydrocyclopenta[b]pyrrole . HCl | 50 mg |
| 1-(3-methylaminopropyl)-2-phenyl-1,4,5,6-tetrahydrocyclopenta[b]pyrrole . oxalate | 25 mg |
| 1-(2-methylaminoethyl)-2-phenyl-1,4,5,6,7,8-hexahydrocyclohepta[b]pyrrole . HCl | 50 mg |
| 1-(3-dimethylaminopropyl)-2-phenyl-1,4,5,6,7,8-hexahydrocyclohepta[b]pyrrole . HCl | 25 mg |
| 1-(3-methylaminopropyl)-2-phenyl-1,4,5,6,7,8-hexahydrocyclohepta[b]pyrrole . HCl | 50 mg |
| 1-(3-diethylaminopropyl)-2-phenyl-1,4,5,6,7,8-hexahydrocyclohepta[b]pyrrole . HCl | 50 mg |
| 1-(2-ethylaminoethyl)-2-phenyl-4,5,6,7,8,9-hexahydrocycloocta[b]pyrrole . oxalate | 25 mg |
| 1-(2-ethylaminoethyl)-2-phenyl-4,5,6,7-tetrahydroindole . oxalate | 25 mg |
| 1-(2-diethylaminoethyl)-2-phenyl-5-t-butyl-4,5,6,7-tetrahydroindole . HCl | 20 mg |
| 1-(2-isopropylaminopropyl)-2-(p-chlorophenyl)-4,5,6,7-tetrahydroindole . HCl | 50 mg |
| 1-[2-(1-piperazinylethyl)]-2-phenyl-4,5,6,7-tetrahydroindole . dioxalate | 10 mg |
| 1-(3-diethylaminopropyl)-2-phenyl-4,5-dihydrobenz[e]-indole | 20 mg |
| 1-(3-dimethylaminopropyl-2-phenyl-4,5-dihydrobenz[e]indole . hydrochloride | 20 mg |
| 1-(1-methyl-2-dimethylaminoethyl)-2-phenyl-1,4,5,6,7,8-hexahydrocyclohepta[b]pyrrole . oxalate | 6 mg |
| 1-(3-methylaminopropyl)-2-(p-methoxyphenyl)-1,4,5,6,7,8-hexahydrocyclohepta[b]pyrrole . oxalate | 10 mg |
| 1-(3-isopropylaminopropyl)-2-phenyl-1,4,5,6,7,8-hexahydrocyclohepta[b]pyrrole . oxalate | 37 mg |
| 1-(3-dimethylaminopropyl)-2-(p-aminophenyl)-4,5,6,7,8,9-hexahydrocycloocta[b]pyrrole . dioxalate | 25 mg |
| 1-(3-dimethylaminopropyl)-2,3-diphenyl-4,5,6,7-tetrahydroindole . oxalate | 25 mg |
| 1-(3-dimethylaminopropyl)-2-(3,4,5-trimethoxyphenyl)-1,4,5,6,7,8-hexahydrocyclohepta[b]pyrrole . HCl | 50 mg |
| 1-(3-dimethylaminopropyl)-2-p-fluorophenyl)-1,4,5,6,7,8-hexahydrocyclohepta[b]pyrrole . HCl | 50 mg |

Table I-continued

| Compound | MED/Kilogram of body weight |
| --- | --- |

The compounds of this invention are useful as antiinflammatory agents because of their ability to suppress inflammation in mammals. The utility of the compounds is demonstrated in the carrageenin-induced rat paw edema antiinflammatory assay [Proc. Soc. Exp. Biol. Med. III, 544 (1962)]. For example, at a dose of 200 mg/kg. of body weight, the compounds shown in Table II below effect the corresponding inhibition of edema Table II

| Compound | % Inhibition of edema |
| --- | --- |
| 1-(3-diethylaminopropyl)-2-phenyl-4,5-dihydrobenz[e]indole . HCl | 72 |
| 1-(3-dimethylaminopropyl)-2-phenyl-4,5-dihydrobenz[e]indole . HCl | 56 |
| 1-(3-dimethylaminopropyl)-2-(p-methoxyphenyl)-4,5,6,7-tetrahydroindole . HCl | 44 |
| 1-(2-methylaminoethyl)-2-(m-trifluoromethylphenyl)-4,5,6,7-tetrahydroindole | 58 |
| 1-(3-diethylaminopropyl)-2-phenyl-1,4,5,6,7,8,-hexahydrocyclohepta[b]pyrrole . HCl | 50 |
| 1-(2-dimethylaminoethyl)-2-phenyl-4,5,6,7-tetrahydroindole . HCl | 47 |
| 1-(3-dimethylaminopropyl)-2-(p-chlorophenyl)-4,5,6,7-tetrahydroindole | 44 |
| 1-(3-dimethylaminopropyl)-2-phenyl-4,5,6,7-tetrahydroindole . HCl | 45 |
| 1-(1-methyl-2-dimethylaminoethyl)-2-(m-trifluoromethylphenyl)-4,5,6,7-tetrahydroindole . HCl | 46 |
| 1-(2-diisopropylaminoethyl)-2-(p-hydroxyphenyl)-4,5,6,7-tetrahydroindole | 44 |
| 1-(3-dimethylaminopropyl)-2-(p-aminophenyl)-4,5,6,7,8,9-hexahydrocycloocta[b]pyrrole | 57 |
| 1-(1-methyl-2-dimethylaminoethyl)-2-phenyl-1,4-5,6,7,8-hexahydrocyclohepta[b]pyrrole . oxalate | 58 |

The compounds of this invention are also useful as antihypertensive agents because of their ability to lower blood pressure in mammals. The activity of these compounds is demonstrated by their ability to lower blood pressure when tested in the spontaneous hypertensive rat by the indirect tail cuff method described in "Methods in Pharmacology," Vol. 1, edited by A. Schwartz, Appleton-Century-Crofts, New York, New York, 1971, p. 135. For example, at a dose of 100 mg/kg of body weight, the compounds shown in Table III below effect the corresponding decrease in systolic blood pressure.

Table III

| Compound | decrease in systolic blood pressure |
| --- | --- |
| 1-(3-dimethylaminopropyl)-2-phenyl-1,4,5,6,7,8-hexahydrocyclohepta[b]pyrrole . HCl | 50 mm Hg |
| 1-(3-dimethylaminopropyl)-2-phenyl-4,5,6,7,8,9-hexahydrocycloocta[b]pyrrole . HCl | 50 mm Hg |
| 1-(3-diethylaminopropyl)-2-phenyl-1,4,5,6,7,8-hexahydrocyclohepta[b]pyrrole . HCl | 49 mm Hg |
| 1-(2-dimethylaminoethyl)-2-phenyl-1,4,5,6,7,8-hexahydrocyclo- | |

Table III-continued

| Compound | decrease in systolic blood pressure |
|---|---|
| cyclohepta[b]pyrrole . HCl | 45 mm Hg |
| 1-(3-methylaminopropyl)-2-phenyl-1,4,5,6,7,8-hexahydro-cyclohepta[b]pyrrole . HCl | 42 mm Hg |
| 4,5-dihydro-1-(3-diethylaminopropyl)-2-phenylbenz[e]indole . HCl | 40 mm Hg |
| 4,5-dihydro-1-(3-dimethylaminopropyl)-2-phenylbenz[e]indole . HCl | 30 mm Hg |
| 5-t-butyl-1-(2-diethylaminoethyl)-2-phenyl-4,5,6,7,-tetrahydroindole . HCl | 30 mm Hg |
| 4,5-dihydro-1-(dimethylaminopropyl)-2-phenylbenz[g]indole . HCl | 24 mm Hg |

Examples of other compounds within the scope of the invention are:

1-(2-isopropylaminoethyl)-2-(3,4-dichlorophenyl)-4,5,6,7-tetrahydroindole 1-(3-methylaminopropyl)-2-phenyl-4,5,6,7-tetrahydroindole 1-(3-dimethylaminopropyl)-2-(p-methoxyphenyl)-4,5,6,7,8,9-hexahydrocycloocta[b]pyrrole 2-(p-bromophenyl)-1-(3-dimethylaminopropyl)-1,4,5,6,7,8-hexahydrocyclohepta[b]pyrrole 2-(p-cyanophenyl)-1-(3-dimethylaminopropyl)-1,4,5,6,7,8-hexahydrocyclohepta[b]pyrrole 1-(3-methylaminopropyl)-2-phenyl-7-chloro-4,5,-dihydrobenz[e]-indole 1-[2-(1-imidazolidonethyl)]-2-phenyl-4,5,6,7-tetrahydroindole 1-(3-diethylaminopropyl)-2-(p-methoxyphenyl)-4,5,6,7,8,9-hexahydrocycloocta[b]pyrrole 1-(4-diethylamino-2-butenyl)-2-phenyl-4,5,6,7-tetrahydroindole hydrochloride The active compounds of the invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspension, syrups, wafers, chewing gum, and the like. The preparations should contain at least 0.5% of active compound, but may be varied depending upon the particular form and may conveniently be between 7% to about 70% of the weight of the unit. The amount of active compound in such compositions is such that a suitable dosage will be obtained. Preferred compositions and preparations according to the present invention are prepared so that an oral dosage unit form contains between 1-250 milligrams of active compound.

The tablets, pills, capsules, troches and the like may also contain: a binder such as hydroxypropyl cellulose, ethyl cellulose, acacia, polyvinyl pyrrolidine, corn starch or gelatin; an excipient such as starch, lactose, sucrose, microcrystalline cellulose, or dibasic calcium phosphate; a disintegrating agent such as alginic acid, potato starch, microcrystalline cellulose, or the like; a lubricant such as magnesium stearate, talc, stearic acid or PEG 6000; a sweetening agent such as sucrose or saccharin; and a flavoring agent such as peppermint, methyl salicylate, or orange flavoring. When the dosage unit form is a capsule, it may also contain a liquid carrier such as a fatty acid. Other dosage unit forms may contain various materials which modify the physical form of the dosage unit, for example, as coatings. Thus, tablets or pills may be coated with sugar, shellac, or cellulose derivatives. A syrup may contain, in addition to the above compounds, sucrose as a sweetening agent, certain preservatives, dyes, colorings, and flavorings. Materials used in preparing these various compositions must be pharmaceutically pure.

The compounds of this invention may also be intravenously administered as sterile aqueous solutions. The pH of these solutions may be adjusted with phosphate or citrate buffers and the solutions may contain preservatives. The solutions should contain at least 0.5% of active compound and may conveniently contain from 1–10% of active compound. The concentration will be such that a suitable dosage will be obtained.

The preferred routes of administering the compounds of this invention to patients are oral and intravenous.

Acids useful for preparing the physiologically tolerable acid addition salts of the compounds of the invention include inorganic acids such as hydrochloric, hydrobromic, sulfuric, nitric, phosphoric and perchloric acids, as well as organic acids such as oxalic, tartaric, citric, acetic, succinic, maleic and ethane disulfonic acids.

The following examples are representative of the compounds of the invention and their preparation.

EXAMPLE I a. A solution of 60.9 g (0.31 mole) of phenacyl bromide in 150 ml. of toluene is added dropwise with stirring to a refluxing solution of 46.6 g of 1-pyrrolidino-1-cyclohexene in 150 ml. of toluene. The mixture is heated under reflux for 2 hours, diluted with 150 ml. of water, refluxed for 3 hours and cooled. The layers are separated and the aqueous phase is extracted with ether. The organic solution is dried and concentrated to an oil. The oil is distilled to give an orange liquid which solidifies. The resulting solid is recrystallized from an ether petroleum mixture to give 2-phenacylcyclohexanone as tan crystals, m.p. 44°–45° C.

b. 5.96 g (0.067 mole) of dimethylaminoethylamine are added dropwise under nitrogen to a stirred solution of 14.6 g (0.067 mole) of 2-phenacylcyclohexanone in glacial acetic acid. After refluxing overnight, water is added and the aqueous solution is extracted with ether. The ether layer is dried and concentrated to an orange oil which solidifies to a light orange solid. The solid is dissolved in ether and ethereal hydrogen chloride is added to give the hydrochloride as a light tan solid. The solid is recrystallized twice from isopropanol and then from methanol-ether to give 1-(2-dimethylaminoethyl)-2-phenyl4,5,6,7-tetrahydroindole hydrochloride as white crystals, m.p. 212°–213.5° C.

Analysis: Calculated for $C_{18}H_{24}N_2 \cdot HCl$: 70.90% C; 8.28% H; 9.19% N Found: 71.00% C; 8.27% H; 9.18% N

EXAMPLES 2–8

Following the manipulative procedure described above in Example 1(b), substituting an appropriate aminoalkylamine for dimethylaminoethylamine produces the corresponding compounds of the invention listed below in Table IV.

Table IV

| Ex | Z | $R_1$ | $R_2$ | $R_1{}^NR_2$ | Recryst'n Solvent | Empirical Formula | M.P. °C | Calculated %C | %H | %N | Found %C | %H | %N |
|----|---|-------|-------|--------------|-------------------|-------------------|---------|---------------|------|------|----------|------|------|
| 2 | $(CH_2)_2$ | H | $CH_3$ | — | MeOH—EtOH | $C_{17}H_{22}N_2 \cdot (CO_2H)_2$ | 206–207 | 66.24 | 7.03 | 8.13 | 66.05 | 6.94 | 7.91 |
| 3 | $(CH_2)_2$ | H | $C_2H_5$ | — | MeOH—$H_2O$ | $C_{18}H_{24}N_2 \cdot (CO_2H)_2$ | 225-dec. | 67.01 | 7.31 | 7.82 | 66.96 | 7.33 | 7.70 |
| 4 | $(CH_2)_2$ | $C_2H_5$ | $C_2H_5$ | — | Isopropanol-$Et_2O$ | $C_{20}H_{28}N_2 \cdot (CO_2H)_2$ | 92–98 | 68.37 | 7.82 | 7.25 | 68.00 | 7.64 | 7.18 |
| 5 | $(CH_2)_2$ | — | — | $\begin{bmatrix} \ \ \ \mid \\ N \\ N \\ \mid \\ H \end{bmatrix}$ | MeOH | $C_{20}H_{27}N_3 \cdot 2(CO_2H)_2$ | 168–170 dec. | 58.88 | 6.38 | 8.58 | 59.23 | 6.46 | 8.60 |
| 6 | $(CH_2)_3$ | $CH_3$ | $CH_3$ | — | Isopropanol | $C_{19}H_{26}N_2 \cdot HCl$ | 219 | 71.55 | 8.55 | 8.79 | 71.43 | 8.63 | 8.67 |
| 7 | $(CH_2)_4$ | $C_2H_5$ | $C_2H_5$ | — | ethylacetate-MeOH | $C_{22}H_{32}N_2 \cdot HCl$ | 147–150 | 73.20 | 9.21 | 7.76 | 73.22 | 9.13 | 7.88 |
| 8 | $CH_2$<br>$\mid$<br>$CH$<br>$\parallel$<br>$CH$<br>$\mid$<br>$CH_2$ | $C_2H_5$ | $C_2H_5$ | — | ethylacetate-$Et_2O$ | $C_{22}H_{30}N_2 \cdot HCl$ | 130 | 73.61 | 8.71 | 7.81 | 73.00 | 8.65 | 7.74 |

EXAMPLE 9

6.5 g (0.05 mole) of imidazolidonylethylamine in glacial acetic acid are added to a stirred solution of 10.8 g (0.05 mole) of 2-phenacylcyclohexanone [Example 1(a)] under nitrogen. After refluxing for 5 hours, the mixture is poured into water and the pH is adjusted to 1 with 2N hydrochloric acid. The aqueous acidic solution is extracted with ether. The ether solution is washed with water and saturated sodium bicarbonate solution and dried over sodium sulfate. Evaporation of the ether gives a tan solid which is recrystallized twice from ether to give 1-[2-(1-imidazolidonylethyl)]-2-phenyl-4,5,6,7-tetrahydroindole, m.p. 129°–131° C.

Analysis: Calculated for $C_{19}H_{23}N_3O$: 73.75% C; 7.49% H; 13.58% N Found: 73.38% C; 7.56% H; 13.48% N

EXAMPLE 10 a. Reacting 33.0 g (0.22 mole) of 1-pyrrolidino-1-cyclohexene with 50 g (0.22 mole) of p-methoxyphenacyl bromide by the method described in Example 1(a) gives 2-(p-methoxyphenacyl) cyclohexanone as crystals, m.p. 98°–99° C.

b. 4.41 g (0.05 mole) of dimethylminoethylamine are added dropwise to a stirred suspension of 12.32 g (0.05 mole) of 2-(p-methoxyphenacyl)cyclohexanone in glacial acetic acid. After refluxing overnight, ice and water are added, and the cloudy mixture is washed with ether. The aqueous solution is basified with 10% sodium carbonate and extracted with ether. Removal of the ether after drying over sodium sulfate gives a light brown oil which solidifies on cooling. The resulting solid is recrystallized from methanol to give 1-(2-dimethylaminoethyl)-2(p-methoxyphenyl)-4,5,6,7-tetrahydroindole as white needles, m.p. 81°–82° C.

Analysis: Calculated $C_{19}H_{26}N_2O$: 76.45% C; 8.80% H; 9.39% N Found: 76.32% C; 8.75% H; 9.50% N

EXAMPLE 11

By following the manipulative procedure of Example 10, substituting dimethylaminopropylamine for dimethylaminoethylamine, the corresponding compound of the invention is prepared. The hydrochloric acid addition salt is prepared and is recrystallized for isopropanol ether to give 1-(3-dimethylaminopropyl)-2-(p-methoxyphenyl)-4,5,6,7-tetrahydroindole hydrochloride as light tan crystals, m.p. 190° C.

Analysis: Calculated for $C_{20}H_{28}N_2O \cdot HCl$: 68.84% C; 8.39% H; 8.03% N Found: 68.30% C; 8.47% H; 7.91% N

EXAMPLE 12

A suspension of 50 g (0.18 mole) of p-bromophenacyl bromide in 215 ml. of toluene is added in small portions to a stirred boiling solution of 27.2 g (0.18 mole) of 1-pyrrolidino-1-cyclohexene in 90 ml. of toluene. The mixture is heated under reflux for 2 hours, diluted with 90 ml. of water and refluxed for 3 hours. The layers are separated and the aqueous phase is extracted with ether. The organic solution is dried over sodium sulfate and concentrated to an oil which solidifies. The solid is recrystallized from a cyclohexane-ethanol mixture to give 2-(p-bromophenacyl)-cyclohexanone as colorless crystals, m.p. 78°–80° C.

b. 4.09 g (0.04 mole) of dimethylaminopropylamine are added dropwise to a stirred suspension of 11.81 g (0.04 mole) of 2-(p-bromophenacyl)cyclohexanone in glacial acetic acid under nitrogen. After refluxing overnight, ice and water are added, and the aqueous solution is washed with ether, made basic with sodium carbonate, and extracted with ether. Removal of the ether from the solution after drying over sodium sulfate gives a reddish brown oil which solidifies to a reddish brown solid. Ethereal hydrogen chloride is added to an ether solution of this solid to give the hydrochloride salt. This is recrystallized from an isopropanol-ether mixture to give 2-(p-bromophenyl)-1-(3-dimethylaminopropyl)-4,5,6,7-tetrahydroindole hydrochloride, m.p. 210°–211° C.

Analysis: Calculated for $C_{19}H_{25}BrN_2 \cdot HCl$: 57.36% C; 6.60% H; 7.04% N Found: 57.04% C; 6.60% N; 6.97% N

EXAMPLE 13

6.5 g (0.05 mole) of N-(2-aminoethyl)morpholine are added dropwise to a stirred mixture of 14.8 g (0.05 mole) of 2-(p-bromophenacyl)cyclohexanone, [Example 12(a)] in glacial acetic acid under nitrogen. After refluxing for 5 hours, the mixture is poured into water and the pH is adjusted to 1 with 2N hydrochloric acid. Upon cooling, a tan solid separates, is collected, and recrystallized twice from methanol to give 2-(p-bromophenyl)-1-[2-(1-morpholinoethyl)]-4,5,6,7-tetrahydroindole hydrochloride, m.p. 240° C. dec.

Analysis: Calculated for $C_{20}H_{25}BrN_2O \cdot HCl$: 56.41% C; 6.16% H; 6.58% N Found: 55.97% C; 6.29% H; 6.40% N

EXAMPLE 14 a. A stirred mixture of 15.9 g (0.11 mole) of 1-pyrrolidino-1-cyclohexene, 28.0 g (0.11 mole) of m-trifluoromethylphenacyl bromide, and 100 ml. of toluene is heated under reflux for 2 hours, diluted with water, and refluxed for 2 hours. The layers are separated, and the organic phase is dried and concentrated to a liquid. Distillation provides 2-(m-trifluoromethylphenacyl)cyclohexanone as a liquid, b.p. 137°–138° C. (0.075 mm).

b. 3.71 g (0.05 mole) of methylaminoethylamine are added dropwise to a stirred solution of 14.22 g (0.05 mole) of 2-(m-trifluoromethylphenacyl)cyclohexanone in glacial acetic acid under nitrogen. After refluxing for 10 hours, water is added and the aqueous solution is washed with ether. The aqueous solution is basified with 10% sodium carbonate and extracted with ether. Drying and concentration gives a brown oil which is dissolved in ether. Ethereal hydrogen chloride is added to give the hydrochloride which is recrystallized from a methanol-ether mixture to give 1-(2-methylaminoethyl)-2-(m-trifluoroethylphenyl)-4,5,6,7-tetrahydroindole hydrochloride as white crystals, m.p. 154°–156° C.

Analysis: Calculated for $C_{18}H_{21}F_3N_2 \cdot HCl$: 60.24% N; 6.19% H; 7.81% N Found: 60.00% N; 6.27% H; 7.81% N

EXAMPLES 15–19

Following the manipulation procedure described above in Example 14(b), substituting an appropriate aminoalkylamine for methylaminoethylamine produces the corresponding compounds of the invention tested below in Table V.

solution is treated with charcoal, dried over sodium sulfate and concentrated to a reddish brown oil that solidifies. The solid is dissolved in ether and ethereal hydrogen chloride added dropwise to form the hydrochloride salt which is recrystallized from a methanol-ether mixture to give 1-(3-dimethylaminopropyl)-2-(p-chlorophenyl)-4,5,6,7-tetrahydroindole hydrochloride, m.p. 213°–214° C.

Analysis: Calculated for $C_{19}H_{25}ClN_2 \cdot HCl$: 64.58% C; 7.43% H; 7.93% N Found: 64.35% C; 7.29% H; 7.86% N

EXAMPLE 21

5.8 g (0.05 mole) of 2-isopropylaminopropylamine are added dropwise to a stirred solution of 12.5 g (0.05 mole) of 2-(p-chloro-phenacyl)cyclohexanone [Example 20(a)] in glacial acetic acid dropwise under nitrogen. After refluxing for 5 hours, the reaction mixture is cooled and poured into 500 ml. of water. The pH is adjusted to 1 with dilute hydrochloric acid, at which point a tan solid separates. This solid is recrystallized from methanol and then twice from an isopropanol-ether mixture to give 1-(2-isopropylaminopropyl)-2-(p-chlorophenyl)-4,5,6,7-tetrahydroindole hydrochloride as tan crystals, m.p. 192°–194° C.

Analysis: Calculated for $C_{20}H_{27}ClN_2 \cdot HCl$: 65.39% C; 7.68% H; 7.63% N Found: 65.44% C; 7.97% H; 7.49% N

EXAMPLE 22 a. 43 g (0.2 mole) of (p-hydroxyphenacyl bromide) are added dropwise during 1/2 hour to a cooled (25° C) solution of 30 g (0.2 mole) of 1-pyrrolidino-1-cyclohexene in dimethylformamide. After 5 1/2 hours, the solution is diluted with water and extracted with chloroform. The chloroform solution is washed with water, dried over sodium sulfate and concentrated to Table V

| Ex | Z | $R_1$ | $R_2$ | Recryst'n Solvent | Empirical Formula | M.P. ° C. | Calculated %C | %H | %N | Found %C | %H | %N |
|---|---|---|---|---|---|---|---|---|---|---|---|---|
| 15 | $(CH_2)_2$ | $CH(CH_3)_2$ | $CH(CH_3)_2$ | Isopropanol-$Et_2O$ | $C_{23}H_{31}F_3N_2 \cdot HCl$ | 145–148 | 64.39 | 7.52 | 6.53 | 64.08 | 7.78 | 6.37 |
| 16 | $(CH_2)_2$ | H | $C_6H_5$ | Isopropanol-$Et_2O$ | $C_{23}H_{23}F_3N_2 \cdot HCl$ | 172–175 | 65.63 | 5.75 | 6.66 | 65.47 | 5.80 | 6.68 |
| 17 | $CH_3-CH$<br>\|<br>$CH_2$ | $CH_3$ | $CH_3$ | Isopropanol-$Et_2O$ | $C_{20}H_{25}F_3N_2 \cdot HCl$ | 175–177 | 62.08 | 6.79 | 7.24 | 62.11 | 6.87 | 7.13 |
| 18 | $(CH_2)_3$ | $CH_3$ | $CH_3$ | Isopropanol-$Et_2O$ | $C_{20}H_{25}F_3N_2 \cdot HCl$ | 168–170 | 62.08 | 6.79 | 7.24 | 61.61 | 6.69 | 7.28 |
| 19 | $CH_2-CH$<br>\|<br>$CH_3$ | $CH_3$ | $CH_3$ | $Et_2O$ | $C_{20}H_{25}F_3N_2 \cdot HCl$ | 145–148 | 62.08 | 6.79 | 7.24 | 61.90 | 6.87 | 7.14 |

EXAMPLE 20 a. The reaction of 69.5 g (0.46 mole) of 1-pyrrolidino-1-cyclohexene and 100 g (0.46 mole) of p-chlorophenacyl bromide by the method described in Example 1(a) gives 2-(p-chlorophenacyl)cyclohexanone as tan crystals, m.p. 56°–58° C.

b. 5.11 g (0.05 mole) of dimethylaminopropylamine are added dropwise to a stirred solution of 12.5 g (0.05 mole) of 2-(p-chlorophenacyl)cyclohexanone in glacial acetic acid under nitrogen. After refluxing for 9 hours and sitting at ambient temperature overnight, water is added and the aqueous solution is washed with ether. The aqueous portion is neutralized with 10% sodium carbonate and extracted with ether. The ether an oil. Distillation gives a liquid which solidifies to give 2-(p-hydroxyphenacyl) cyclohexanone, m.p. 120°–125° C.

b. A solution of 7.25 g (0.071 mole) of isopropylaminoethylamine, 16.5 g (0.071 mole) of 2-(p-hydroxyphenacyl)cyclohexanone and acetic acid is refluxed under nitrogen for 6 hours, then cooled to ambient temperature, and diluted with water. The aqueous solution is washed with ether, then basified with 10% sodium carbonate and extracted with chloroform. The chloroform solution is washed with saturated sodium chloride solution, treated with charcoal, and dried over magnesium sulfate. The chloroform is removed to give a yellow solid which is recrystallized from acetonitrile to give a yellow-tan solid. The solid is dissolved in ether, the solution is filtered and concentrated to give 2-(p-hydroxyphenyl-1-(2-isopropylaminoethyl)-4,5,6,7-tetrahydroindole as a pale yellow solid, m.p. 149°–150° C.

Analysis: Calculated for $C_{19}H_{26}N_2O$: 76.45% C; 8.79% H; 9.38% N Found: 76.17% C; 8.80% H; 9.17% N

EXAMPLE 23

A solution of 5.77 g (0.04 mole) of diisopropylaminoethylamine and 9.3 g (0.04 mole) of 2-(p-hydroxyphenacyl) cyclohexanone in glacial acetic acid is refluxed under nitrogen for 14 hours, then cooled to ambient temperature and diluted with water and dilute hydrochloric acid. The aqueous solution is washed with ether, basified with 10% sodium carbonate and extracted with ether. After drying the ether solution over magnesium sulfate, the ether is removed to give a pale yellow solid. The solid is recrystallized from an ether-petroleum ether mixture to give pale yellow crystals of 1-(2-diisopropylaminoethyl)-2-(p-hydroxyphenyl)-4,5,6,7-tetrahydroindole as pale yellow crystals, m.p. 112°–114.5° C.

Analysis: Calculated for: $C_{22}H_{32}N_2O$: 77.58% C; 9.49% H; 8.23% N Found: 77.49% C; 9.45% H; 8.11% N

EXAMPLE 24 a. Reaction of 72.5 g (0.44 mole) of 4-methyl-1-pyrrolidino-1-cyclohexene and 87.6 g (0.44 mole) of phenacyl bromide by the method described in Example 22(a) gives 4-methyl-2-phenacylcyclohexanone as a viscous oil.

b. A solution of 5.94 g (0.05 mole) of 2-diethylaminoethylamine and 11.52 g (0.05 mole) of 4-methyl-2-phenacyl-cyclohexanone in glacial acetic acid is refluxed under nitrogen for 8 hours. Water is added to the mixture, and the mixture is acidified with dilute hydrochloric acid and washed with ether. The aqueous solution is basified with 10% sodium carbonate and extracted with ether to give a light brown oil. The oil is dissolved in ether and ethereal hydrogen chloride is added to give a granular off-white salt. The salt is recrystallized from an isopropanol-ether mixture and then from a methanol-ether pair to give 1-(2-diethylaminoethyl)-2-phenyl-5-methyl-4,5,6,7-tetrahydroindole hydrochloride as light tan crystals, m.p. 171°–177° C.

Analysis: Calculated for $C_{21}H_{30}N_2.HCl$: 72.69% C; 9.02% H; 8.08% N Found: 72.70% C; 9.00% H; 8.01% N

EXAMPLE 25 a. Reaction of 61.0 g (0.30 mole) of 4-(t-butyl)-1-pyrrolidino-1-cyclohexene and 59.7 g (0.30 mole) of phenacyl bromide by the method described in Example 22(a) gives a solid. The solid is recrystallized from ethanol to give 4-(t-butyl)-2-phenacylcyclohexanone, m.p. 127°–129° C.

b. 4.6 g (0.04 mole) of diethylaminoethylamine are added dropwise to a stirred solution of 10.9 g (0.04 mole) of 4-(t-butyl)-2-phenacylcyclohexanone in glacial acetic acid under nitrogen. After refluxing for 5 hours, ice and water are added, and the aqueous solution is washed with ether. The aqueous extract is basified with 10% sodium carbonate solution and extracted with ether. The ether solution is dried over sodium sulfate and concentrated to a brown oil. Upon cooling the oil solidifies to tan crystals. The solid is converted to the hydrochloride salt, which is recrystallized from an isopropanol-ether mixture to produce 1-(2-diethylaminoethyl)-2-phenyl-5-(t-butyl)-4,5,6,7-tetrahydroindole hydrochloride, m.p. 202°–204° C.

Analysis: Calculated for $C_{24}H_{36}N_2.HCl$: 74.09% C; 9.59% H; 7.20% N Found: 74.02% C; 9.77% H; 7.52% N

EXAMPLE 26 a. Reaction of 61.4 g (0.31 mole) of phenacyl bromide and 55.7 (0.31 mole) of 4-methoxy-1-pyrrolidino-1-cyclohexene by the method described in Example 22(a) gives 4-methoxy-2-phenacyl-cyclohexanone as an amber oil.

b. 5.8 g (0.05 mole) of diethylaminoethylamine are added dropwise to a stirred solution of 12.3 g (0.05 mole) of 4-methoxy-2-phenacylcyclohexanone in glacial acetic acid under nitrogen. After refluxing for 5 hours, ice and water are added and the aqueous solution is washed with ether. The ether solution is dried over sodium sulfate and concentrated to a brown oil. The oil is converted to the oxalate salt which is recrystallized from methanol to give 1-(2-diethylaminoethyl)-2-phenyl-5-methoxy-4,5,6,7-tetrahydroindole oxalate as tan crystals, dec. 172°–176° C.

Analysis: Calculated for $C_{21}H_{30}N_2O.(CO_2H)_2$: 66.32% C; 7.75% H; 6.73% N Found: 65.81% C; 7.89% H; 6.58% N

EXAMPLE 27 a. Reaction of 28.7 g (0.19 mole) of 1-pyrrolidino-1-cyclohexene and 51.2 g (0.19 mole) of 3,4-dichlorophenacyl bromide by the method described in Example 22(a) gives crystals of 2-(3,4-dichlorophenacyl)-cyclohexanone. Recrystallization from ethanol provides crystals, m.p. 78°–79° C.

b. 2.9 g (0.028 mole) of isopropylaminoethylamine are added dropwise to a stirred solution of 8.0 g (0.028 mole) of 2-(3,4-dichlorophenacyl)cyclohexanone in glacial acetic acid under nitrogen. After refluxing for 5 hours, ice and water are added and the pH of the aqueous solution is adjusted to 1 with dilute hydrochloric acid. The aqueous solution is washed with ether. The aqueous phase is made basic with sodium carbonate and extracted with ether. The ether solution is dried over sodium sulfate and concentrated to off-white solid, which is recrystallized twice from a methanol-ether mixture to give 1-(2-isopropylaminoethyl)-2-(3,4-dichlorophenyl)-4,5,6,7-tetrahydroindole hydrochloride as crystals, m.p. 207°–210° C.

Analysis: Calculated for $C_{19}H_{24}Cl_2N_2.HCl$: 58.85% C; 6.50% H; 7.23% N Found: 58.89% C; 6.64% H; 7.16% N

EXAMPLE 28 a. Reaction of 75.0 g (0.5 mole) of 1-pyrrolidino-1-cyclohexene and 68.7 g (0.25 mole) of α-phenylphenacyl bromide by method described in Example 22(a) gives a colorless semi-solid of 2-(α-phenylphenacyl)-cyclohexanone.

b. 5.1 g (0.05 mole) of dimethylaminopropylamine are added dropwise to a stirred solution of 14.6 g (0.05 mole) of 2-(α-phenylphenacyl)cyclohexanone in glacial acetic acid under nitrogen. After refluxing for 5 hours, ice and water are added, and the aqueous solution is washed with ether. The aqueous solution is basified with a saturated sodium carbonate solution and extracted with ether. The ether solution is washed with water, dried over sodium sulfate and concentrated to a dark oil. An oxalate salt is made of the oil and is recrystallized from an isopropanol-water-ether mixture to give 1-(3-dimethylaminopropyl)-2,3-diphenyl-4,5,6,7-tetrahydroindole oxalate monohydrate, dec. 211° C.

Analysis: Calculated for $C_{25}H_{30}N_2.(CO_2H)_2.H_2O$: 69.50% C; 7.35% H; 6.01% H Found: 69.38% C; 7.22% H; 6.31% H

EXAMPLE 29 a. Reaction of 18.1 g (0.12 mole) of 1-pyrrolidino-1-cyclohexene and 25.0 g (0.12 mole) of p-fluorophenacyl bromide by the method described in Example 1(a) gives 2-(p-fluorophenacyl)cyclohexanone as a solid.

b. 5.1 G (0.04 mole) of 3-(1-pyrrolidino) propylamine are added dropwise to a stirred solution of 9.4 g (0.04 mole) of 2-(p-fluorophenacyl)cyclohexanone in glacial acetic acid. After refluxing for 5 hours, ice and water are added and the solution is washed with ether. The aqueous portion is basified with saturated sodium carbonate, and then extracted with ether. The ether layer is washed with water, dried over sodium sulfate, and concentrated to a yellow oil which is converted to a hydrochloride salt. The salt is recrystallized twice from an isopropanol-ether mixture to give 1-[3-(1-pyrrolidinopropyl)]-2-(p-fluorophenyl)-4,5,6,7-tetrahydroindole hydrochloride, m.p. 209°–211° C.

Analysis: Calculated for $C_{21}H_{27}FN_2.HCl$: 69.50% C; 7.78% H; 7.22% N Found: 69.35% C; 7.74% H; 7.78% N

EXAMPLE 30 a. A solution of 20.1 g (0.1 mole) of phenacyl bromide in 65 ml. of dry toluene is added dropwise during 30 minutes to a stirred refluxing solution of 20.2 g (0.1 mole) of 1-(1-pyrrolidino)-3,4-dihydronapthalene and 50 ml. of toluene. The reaction mixture is heated under reflux for 6 hours, diluted with 50 ml. of water, refluxed for 4 hours and cooled. The layers are separated and the aqueous phase is extracted with benzene. The organic solution is dried over sodium sulfate and concentrated to a semi-solid. The semi-solid is triturated with cold 30°–60° petroleum ether to give a solid. The solid is recrystallized from 30°–60° petroleum ether to give a solid. The solid is recrystallized from 30°–60° petroleum ether to give 2-phenacyl-1-tetralone as crystals, m.p. 87°–88° C.

b. 5.11 g (0.05 mole) of dimethylaminopropylamine are added dropwise to a stirred suspension of 13.21 g (0.05 mole) of 2-phenacyl-1-tetralone in glacial acetic acid. After 5 hours reflux, Addition of ice and water gives a brown precipitate which is filtered off, and the aqueous filtrate is washed with ether. The aqueous solution is basified with 10% sodium carbonate and extracted with ether. The ether solution is treated with charcoal, dried over sodium sulfate and concentrated to a dark brown oil. The oil is dissolved in ether and ethereal hydrogen chloride is added to give the solid hydrochloride. The salt is recrystallized twice from a methanol-ether mixture to give 1-(3-dimethylaminopropyl)-2-phenyl-4,5-dihydrobenz[g]indole hydrochloride, m.p. 172°–175° C.

Analysis: Calculated for $C_{23}H_{26}N_2.HCl$: 75.27% C; 7.43% H; 7.64% N Found: 75.11% C; 7.31% H; 7.81% N

EXAMPLE 31 a. 20 g (0.1 mole) of phenacyl bromide and 65 ml. of toluene are added dropwise during 30 minutes to a refluxing stirred solution of 20 g (0.1 mole) of 1-(3,4-dihydro-2-napthyl)pyrrolidine and 50 ml. of toluene. The mixture is heated under reflux for 3 hours, diluted with 50 ml. of water, refluxed for 4 hours and cooled. The layers separate, the aqueous phase is extracted with benzene, the organic solution is dried and concentrated to an oil. The oil is crystallized from a 30°–60° petroleum ether-ether mixture to give 1-phenacyl-2-tetralone as tan crystals, m.p. 48°–52° C.

b. 2.6 g (0.026 mole) of dimethylaminopropylamine are added dropwise to a stirred solution of 7.0 g (0.026 mole) of 1-phenacyl-2-tetralone in glacial acetic acid under nitrogen. After refluxing for 5 hours, ice and water are added, and the aqueous solution is washed with ether. The aqueous portion is basified with saturated sodium carbonate solution, then extracted with ether. The ether solution is washed with water, dried over sodium sulfate and concentrated to a dark oil. The oil is converted into a hydrochloride salt which is recrystallized twice from an isopropanolether mixture to give 1-(3-dimethylaminopropyl)-2-phenyl-4,5-dihydrobenz[e]indole hydrochloride, m.p. 185°–187° C.

Analysis: Calculated for $C_{23}H_{26}N_2.HCl$: 75.28% C; 7.42% H; 7.64% N Found: 75.36% C; 7.49% H; 7.69% N

EXAMPLE 32

By following the manipulative procedure described above in Example 31(b), substituting diethylaminopropylamine for dimethyl aminopropylamine, gives 1-(3-diethylaminopropyl)- 4,5-dihydro-2-phenylbenz[e]indole hydrochloride, m.p. 173-176° C.

Analysis: Calculated for $C_{25}H_{30}N_2.HCl$: 76.02% C; 7.91% H; 7.09% N Found: 76.26% C; 8.29% H; 7.09% N

EXAMPLE 33 a. Reaction of 28.0 g (0.12 mole) of 6-chloro-3,4-dihydro-2-pyrrolidinonapthalene and 24.0 g (0.12 mole) of phenacyl bromide by the method described in Example 22(a) gives 6-chloro-1-phenacyl-2-tetralone as a brown oil.

b. 4.4 g (0.05 mole) of methylaminopropylamine are added dropwise to a stirred solution of 14.8 g (0.05 mole) of 6-chloro-1-phenacyl-2-tetralone in glacial acetic acid. After refluxing for 5 hours, ice and water are added and the solution is washed with ether. The aqueous phase is basified with saturated sodium carbonate solution and extracted with ether. The ether layer is washed with water, dried and concentrated to a dark oil. The oil is converted to a hydrochloride salt which is recrystallized twice from an isopropanol-ether mixture to give 1-(3-methyl-aminopropyl)-2-phenyl-7-chloro-4,5-dihydrobenz[e] indole hydrochloride, m.p. 183° C.

Analysis: Calculated for $C_{22}H_{23}ClN_2.HCl$: 68.21% C; 6.25% H; 7.23% N Found: 67.85% C; 6.59% H; 6.79% N

EXAMPLE 34 a. A solution of 72.4 g (0.36 mole) of phenacyl bromide in 175 ml. of toluene is added dropwise to a stirred boiling solution of 50 g (0.036 mole) of 1-pyrrolidino-1-cyclopentene and 200 ml. of toluene. The reaction mixture is heated under reflux for 3 hours. diluted cautiously with 200 ml. of water, refluxed for 4 hours and cooled. After the layers separate, the aqueous phase is extracted with benzene, and the organic phase is dried and concentrated to an oil. Distillation gives 2-phenacylcyclopentanone as a liquid, b.p. 138°–140° C. (0.05 mm).

b. 8.82 g (0.1 mole) of methylaminopropylamine are added to a solution of 20.35 g (0.1 mole) of 2-phenacylcyclopentanone in glacial acetic acid under nitrogen. After refluxing for 12 hours, water is added and the aqueous solution is washed with ether. The aqueous phase is basified with sodium carbonate and extracted with ether to give a reddish oil. The oil is dissolved in ether and is added to an ether solution of oxalic acid to give 1-(3-methylaminopropyl)-2-phenyl-1,4,5,6-tetrahydrocyclopenta[b]pyrrole oxalate, m.p. 184°–185° C.

with ether. The aqueous extract is basified with 10% sodium solution and extracted with ether. The ether solution is dried, and the ether is removed to give a brown oil. The oil is converted to the solid hydrochloride salt which is recrystallized twice from a methanol-ether mixture to yield 1-(2-methylaminoethyl)-2-phenyl-1,4,5,6,7,8-hexahydrocyclohepta[b]pyrrole hydrochloride, dec. at 230° C.

Analysis: Calculated for $C_{18}H_{24}N_2 \cdot HCl$: 70.92% C; 8.27% H; 9.19% N Found: 70.72% C; 8.41% H; 9.07% N

EXAMPLES 37–44

By following the manipulative procedure described above in Example 36(b), substituting an appropriate aminoalkylamine for methylaminoethylamine produces the corresponding compounds of the invention listed below in Table VI.

Table VI

| Ex | Z | $R_1$ | $R_2$ | $\begin{array}{c}N\\/\ \backslash\\R_1\ \ R_2\end{array}$ | Recryst'n Solvent | Empirical Formula | M.P. °C. | Calculated %C | Calculated %H | Calculated %N | Found %C | Found %H | Found %N |
|---|---|---|---|---|---|---|---|---|---|---|---|---|---|
| 37 | $(CH_2)_2$ | $CH_3$ | $CH_3$ | — | MeOH—$Et_2O$ | $C_{19}H_{26}N_2 \cdot HCl$ | 210-dec. | 71.56 | 8.53 | 8.78 | 71.82 | 8.54 | 8.92 |
| 38 | $CH_3{-}CH\atop\vert\ \ \ \ \ \ \ \ \atop CH_2$ | $CH_3$ | $CH_3$ | — | MeOH—$Et_2O$ | $C_{20}H_{28}N_2 \cdot (CO_2H)_2$ | 175-dec. | 68.37 | 7.82 | 7.25 | 68.42 | 7.67 | 7.07 |
| 39 | $(CH_2)_3$ | H | $CH_3$ | — | MeOH—$Et_2O$ | $C_{19}H_{26}N_2 \cdot HCl$ | 189–191 | 71.56 | 8.53 | 8.78 | 71.86 | 8.72 | 8.70 |
| 40 | $(CH_2)_3$ | $CH_3$ | $CH_3$ | — | MeOH—$Et_2O$ | $C_{20}H_{28}N_2 \cdot HCl$ | 195-dec. | 72.16 | 8.78 | 8.41 | 71.91 | 8.85 | 8.44 |
| 41 | $(CH_2)_3$ | $C_2H_5$ | $C_2H_5$ | — | MeOH $Et_2O$ | $C_{22}H_{32}N_2 \cdot HCl$ | 171–173 | 73.20 | 9.22 | 7.76 | 73.60 | 9.50 | 7.64 |
| 42 | $(CH_2)_3$ | H | $C_2H_5$ | — | Isopropanol-$Et_2O$ | $C_{20}H_{28}N_2 \cdot HCl$ | 178-dec. | 72.15 | 8.78 | 8.42 | 72.24 | 8.79 | 8.32 |
| 43 | $(CH_2)_3$ | H | $CH(CH_3)_2$ | — | MeOH—$Et_2O$ | $C_{21}H_{30}N_2 \cdot (CO_2H)_2$ | 217-dec. | 68.97 | 8.05 | 7.00 | 68.72 | 8.08 | 6.78 |
| 44 | $(CH_2)_3$ | — | — | 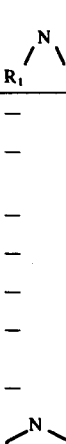 | Isopropanol | $C_{22}H_{30}N_2 \cdot HCl$ | 202–205 | 73.61 | 8.71 | 7.81 | 73.64 | 8.94 | 7.80 |

Analysis: Calculated for $C_{17}H_{22}N_2 \cdot (CO_2H)_2$: 66.25% C; 7.04% H; 8.13% N Found: 66.46% C; 7.10% H; 8.04% N

EXAMPLE 35

By following the manipulative procedure described above in Example 34, substituting dimethylaminopropylamine for methylaminopropylamine gives the corresponding compound of this invention. The hydrochloride salt is made and is recrystallized from isopropanol and then a methanol-ether mixture to give 1-(3-dimethylaminopropyl)-2-phenyl-1,4,5, 6-tetrahydrocyclopenta[b]pyrrole hydrochloride, m.p. 188°–189° C.

Analysis:
Calculated for $C_{18}H_{24}N_2 \cdot HCl$: 70.90% C; 8.28% H; 9.19% N Found: 70.52% C; 8.32% H; 9.57% N

EXAMPLE 36 a. Reaction of 64.1 g (0.4 mole) of 1-pyrrolidino-1-cycloheptene and 79.2 g (0.4 mole) of phenacyl bromide by the method described in Example 1 (a) gives 2-phenacylcycloheptanone as tan crystals, m.p. 42°–44° C.

b. 3.7 g (0.05 mole) of methylaminoethylamine are added dropwise to a stirred solution of 12.1 g (0.05 mole) of 2-phenacylcycloheptanone in glacial acetic acid under nitrogen. After refluxing for 5 hours, ice and water are added, and the aqueous solution is washed

EXAMPLE 45 a. A solution of 106.8 g (0.4 mole) of m-trifluoromethylphenacyl bromide in dry dimethylformamide is added dropwise to a cooled solution of 74.4 g (0.45 mole) of 1-pyrrolidino-1-cycloheptene in dry dimethylformamide. After stirring at ambient temperature for 5 hours, water is added and the mixture is stirred overnight. The reaction mixture is poured into 1500 ml. of water and extracted with chloroform. The chloroform solution is washed with water, dried, and concentrated to a red oil, which is stirred at 60° C. for 1 hour in a high vacuum. Upon cooling, the oil solidifies to an orange solid of 2-(m-trifluoromethylphenacyl)cycloheptanone, m.p. 55°–60° C. The above structure is consistent with infra red and nuclear magnetic resonance spectra.

b. 7.4 (0.1 mole) of methylaminoethylamine are added dropwise to a stirred solution of 29.8 g (0.1 mole) of 2-(m-trifluoromethylphenacyl)cycloheptanone in glacial acetic acid under nitrogen. After refluxing for 5 hours, ice and water are added, and the aqueous solution is washed with ether. The aqueous extract is basified with sodium carbonate solution and extracted with ether. The ether solution is dried, and the ether is removed to give a brown oil. The oil is converted to the hydrochloride salt which is recrystallized twice from isopropanol to give 1-(2-methylaminoethyl)-2-(m-trifluoromethylphenyl)-1,4,5,6,7,8-hexahydrocyclohepta[b]pyrrole hydrochloride, m.p. 155°–158° C.

Analysis: Calculated for $C_{19}H_{23}F_3N_2.HCl$: 61.20% C; 6.49% H; 7.51% N Found: 60.94% C; 6.43% H; 7.59% N

EXAMPLES 46 and 47 a. By following the manipulative procedure described above in Example 45(b), substituting an appropriate aminoalkylamine for methylaminoethylamine produces the corresponding compounds of the invention listed below in Table VII.

Table VII

| Ex | Z | $R_1$ | $R_2$ | Empirical Formula | M.P. ° C | | Analysis % C | % H | % N |
|----|---|-------|-------|-------------------|----------|---|------|-----|-----|
| 46 | $(CH_2)_2$ | $CH_3$ | $CH_3$ | $C_{20}H_{25}F_3N_2 . HCl$ | 202–205 dec. | Calc. | 62.09 | 6.77 | 7.24 |
|    |   |       |       |                   |          | Found | 62.00 | 6.89 | 7.15 |
| 47 | $(CH_2)_3$ | $C_2H_5$ | $C_2H_5$ | $C_{22}H_{31}F_3N_2 . HCl$ | 157–160 | Calc. | 64.40 | 7.52 | 6.53 |
|    |   |       |       |                   |          | Found | 64.65 | 7.57 | 6.45 |

EXAMPLE 48 a. A solution of 44.4 g (0.194 mole) of p-methoxyphenacyl bromide in dry dimethylformamide is added dropwise to a cooled solution of 32 g (0.194 mole) of 1-pyrrolidino-1-cycloheptene in dry dimethylformamide. After stirring at ambient temperature for 48 hours, 500 ml. of water are added and the mixture is stirred for 3 hours. The reaction mixture is poured into 1500 ml. of water and extracted with chloroform. The chloroform solution is washed with water, dried, and concentrated to a red oil which is stirred at 100° C for one hour under a high vacuum. Upon cooling the oil solidifies to a tan solid, m.p. 66°–68° C, of 2-(p-methoxyphenyl)cycloheptanone.

b. 5.1 g (0.05 mole) of dimethylaminopropylamine are added dropwise to a stirred solution of 13.0 g (0.05 mole) of 2-(p-methoxyphenyl)cycloheptanone in glacial acetic acid under nitrogen. After refluxing for 5 hours, ice and water are added, and the aqueous solution is washed with ether. The aqueous phase is basified with sodium carbonate solution and extracted with ether, and the ether solution is dried. Evaporation of the ether leaves a brown oil. The oil is converted to a hydrochloride salt, which is recrystallized from an isopropanol-ether mixture to yield 1-(3-dimethylaminopropyl)-2-(p-methoxyphenyl)-1,4,5,6,7,8-hexahydrocyclohepta[b]pyrrole hydrochloride, m.p. 176°–177° C.

Analysis: Calculated for $C_{21}H_{30}N_2O.HCl$: 69.49% C; 8.16% H; 7.72% N Found: 69.69% C; 8.66% H; 7.57% N

EXAMPLE 49

By following the manipulative procedure described above in Example 48(b), substituting methylaminopropylamine for dimethylaminopropylamine, produces the corresponding compound of the invention. The compound is converted to an oxalate salt which is recrystallized from a methanol - ether mixture to give 1-(3-methylaminopropyl)-minopropyl)-2-(p-methoxyphenyl)-1,4,5,6,7,8-hexahydrocyclohepta[b]-pyrrole oxalate, dec. at 210° C.

Analysis: Calculated for $C_{20}H_{28}N_2O.(CO_2H)_2$: 65.65% C; 7.51% H; 6.96% N. Found: 65.31% C; 7.37% H; 6.94% N.

EXAMPLE 50 a. A solution of 80 g (0.28 mole) of p-bromophenacyl bromide in dry dimethylformamide is added dropwise to a cooled solution of 40.2 g (0.28 mole) of 1-pyrrolidino-1-cycloheptene in dry dimethylformamide. After stirring at ambient temperature for 24 hours, and at 100° C. for 5 hours, water is added and the mixture is stirred for an additional 4 hours. The reaction mixture is poured into 1500 ml. of water and extracted with chloroform. The chloroform solution is washed with water, dried, and evaporated to a red oil which is stirred at 100° for 1 hour under a high vacuum. Upon cooling the oil converts to a semi-solid. The semi-solid is crystallized from an ethanol - cyclohexane mixture to give 2-(p-bromophenacyl)cycloheptanone, m.p. 124°–127° C.

b. A mixture of 18.6 (0.06 mole) of 2-(p-bromophenacyl)cycloheptanone and 6.19 g (0.06 mole) of dimethylaminopropylamine is dissolved in 200 ml. of absolute ethanol. A few drops of concentrated hydrochloric acid are added and the mixture is refluxed for 4 hours. The ethanol is evaporated, and the residue is dissolved in dilute hydrochloric acid and washed with ether. The aqueous solution is basified with sodium carbonate solution and extracted with ether. The ether solution is washed with water, dried, and concentrated to a brown oil which solidifies upon cooling. The resulting solid is recystallized from petroleum ether to give 1-(3-dimethylaminopropyl)-2-(p-bromophenyl)1,4,5,6,7,8-hexahydrocyclohepta[b]pyrrole, m.p. 69–70° C.

Analysis:
Calculated for $C_{20}H_{27}BrN_2$: 63.99% C; 7.25% H; 7.46% N. Found: 64.57% C; 7.37% H; 7.38% N.

EXAMPLE 51

A mixture of 17 g (0.045 mole) of 2-(p-bromophenyl)-1-(3-dimethylaminopropyl)-1,4,5,6,7,8-hexahydrocyclohepta[b]pyrrole(Example 50), and 4.5 g (0.05 mole) of cuprous cyanide is refluxed at 150° in dimethylformamide for 18 hours. The reaction is cooled and poured into a 20% aqueous solution of sodium cyanide. The solution is stirred for a few minutes, diluted with water, and extracted with ether. The combined ether solutions are washed with diluted sodium cyanide solution, water, and then dried. The ether is removed, leaving a brown oil which solidifies upon cooling to a tan solid. The solid is recrystallized twice from a petroleum ether - ether mixture to give 1-(3-dimethylamino-propyl)-2-(p-cyanophenyl)-1,4,5,6,7,8-hexahydrocyclohepta[b]pyrrole, m.p. 96–97° C.

Analysis:
Calculated for $C_{21}H_{27}N_3$: 78.46% C; 8.47% H; 13.07% N.
Found: 77.93% C; 8.36% H; 12.78% N.

EXAMPLE 52 a. By following the manipulative procedure described above in Example 50(a), substituting p-nitrophenacylbromide for p-bromophenacylbromide gives 2-(p-nitrophenacyl)cycloheptanone, m.p. 79°–84° C.

b. 2.2 g (0.022 mole) of dimethylaminopropylamine are added dropwise to a stirred solution of 6.0 g (0.022 mole) of 2-(p-nitrophenacyl)cycloheptanone in glacial acetic acid under nitrogen. After refluxing for 5 hours, the reaction is poured into water, and the aqueous solution is washed with ether. The aqueous solution is basified with sodium carbonate solution and extracted with ether. The ether extract is washed with water, dried, and concentrated to a dark oil which solidifies upon cooling. This solid is converted to a hydrochloric salt which is recrystallized from an isopropanol - ether mixture to give 1-(3-dimethylaminopropyl)-2-(p-nitrophenyl)-1,4,5,6,7,8-hexahydrocyclohepta[b]pyrrole hydrochloride, dec. at 238° C.

Analysis:
Calculated for $C_{20}H_{27}N_3O.2HCl$: 63.56% C; 7.47% H; 11.12% N. Found: 63.43% C; 7.59% H; 10.92% N.

EXAMPLE 53

3.0 g (0.009 mole) of 1-(3-dimethylaminopropyl)-2-(p-nitrophenyl)-1,4,5,6,7,8-hexahydrohepta[b]pyrrole, the free base of Example 52), is dissolved in glacial acetic acid and hydrogenerated in a Paar Hydrogenator with 0.25 g Pd/C for 2 hours. The solution is filtered, poured into water, and washed with ether. The aqueous solution is basified with sodium carbonate solution, then extracted with ether. The ether solution is washed with water, dried, and concentrated to a brown oil. The oil is converted to an oxalate salt which is recrystallized twice from a methanol-water-ether mixture to give 1-(3-dimethylaminopropyl)-2-(p-aminophenyl)-1,4,5,6,7,8-hexahydrocyclohepta[b]pyrrole dioxalate dihydrate, dec. at 140° C.

Analysis:
Calculated for $C_{20}H_{29}N_3.2(CO_2H)_2.2H_2O$: 54.85% C; 6.71% H; 8.00% N. Found: 55.23% C; 6.26% H; 7.62% N.

EXAMPLE 54 a. A solution of 38 g (0.13 mole) of 3,4,5-trimethoxyphenacyl bromide in 150 ml. dry dimethylformamide is added dropwise to a cooled solution of 25 g (0.13 mole) of 1-pyrrolidino-1-cycloheptene in 150 ml. of dry dimethylformamide. After stirring at ambient temperature for 20 hours, 250 ml. of water are added and the mixture is stirred for an additional 3 hours. The reaction mixture is poured into 1500 ml. of water, and tan crystals m.p. 103°–105° C of 2-(3,4,5-trimethoxyphenacyl)cycloheptanone precipitate.

b. 5.1 g (0.05 mole) of dimethylaminopropylamine are added dropwise to a stirred solution of 15.0 g (0.05 mole) of 2-(3,4,5-trimethoxyphenacyl)cycloheptanone in glacial acetic acid under nitrogen. After refluxing for 5 hours, the reaction is poured into water, and the aqueous solution is washed with ether, basified with sodium carbonate solution, and then extracted with ether. The ether solution is washed with water, dried, and concentrated to a brown oil. The oil is converted to a hydrochloride salt and recrystallized from an isopropanol-ether mixture to give 1-(3-dimethylaminopropyl)-2-(3,4,5-trimethoxyphenyl)-1,4,5,6,7,8-hexahydrocyclohepta[b]pyrrole hydrochloride, dec. at 206°–207° C.

Analysis: Calculated for $C_{23}H_{34}N_2O_3$ HCl: 65.30% C; 8.34% H; 6.62% N. Found: 65.05% C; 8.54% H; 6.57% N.

EXAMPLE 55 a. A solution of 32,6 g (0.15 mole) of p-fluorophenacylbromide in 100 ml. of dry dimethylformamide is added dropwise to a cooled solution of 25 g (0.15 mole) of 1-pyrrolidino-1-cycloheptene in 100 ml. of dry dimethylformamide. After stirring at ambient temperature for 20 hours, and at 100° C. for 5 hours, 250 ml. of water are added, and the mixture is stirred for 3 hours. The reaction mixture is poured into 1500 ml. of water, extracted with chloroform, and the chloroform extract is washed with water and dried. Removal of the chloroform leaves 2-(p-fluorophenacyl)cycloheptanone as an oil. Infrared and nuclear magnetic resonance spectra confirm the above structure.

b. 1.7 g (0.017 mole) of dimethylaminopropylamine are added dropwise to a stirred solution of 4.1 g (0.017 mole) of 2-(p-fluorophenacyl)cycloheptanone in glacial acetic acid. After refluxing for 5 hours, ice and water are added, and the aqueous solution is washed with ether. The aqueous solution is basified with sodium carbonate solution, then extracted with ether. The ether solution is washed with water, dried, and concentrated to a brown oil which solidifies upon cooling. The solid is converted into a hydrochloride salt and recrystallized twice from an isopropanol ether mixture to give 1-(3-dimethylaminopropyl)-2-(p-fluorophenyl)-1,4,5,6,7,8-hexahydrocyclohepta[b]pyrrole hydrochloride, m.p. 209°–211° C.

Analysis: Calculated for $C_{20}H_{27}FN_2.HCl$: 68.45% C: 8.04% H; 7.99% N. Found: 67.95% C; 7.80% H; 7.90% N.

EXAMPLE 56 a. A solution of 33.4 g (0.167 mole) of phenacylbromide in 150 ml. of dimethylformamide is added dropwise to a cooled solution of 30 g (0.167 mole) of 1-pyrrolidinocyclooctene in 125 ml of dry dimethylformamide. After stirring at ambient temperature for 2 days and at 80° C. for 4 hours, 200 ml. of water are added, and the mixture is stirred for 2 hours, poured into 1500 ml. of water and extracted with chloroform. The chloroform is washed with water, dried, and evaporated, leaving an orange oil. The oil is stirred at 100° C. for 1 hour under a high vacuum. Upon cooling the oil solidifies to a tan solid, m.p. 68°–70° C., of 2-phenacylcyclooctanone.

b. 5.1 g. (0.05 mole) of dimethylaminopropylamine are added dropwise to a stirred solution of 12.2 g. (0.05 mole) of 2-phenacylcyclooctanone in glacial acetic acid under nitrogen. After refluxing for 5 hours, ice and water are added, and the aqueous solution is washed with ether. The aqueous solution is basified with sodium carbonate solution and extracted with ether. The ether solution is washed with water, dried, and evaporated, leaving a brown oil. The oil is converted to a hydrochloride salt, which is recrystallized twice from an isopropanol - ether mixture to give 1-(3-dimethylaminopropyl)-2-phenyl-4,5,6,7,8,9-hexahydrocycloocta[b]pyrrole hydrochloride, dec. at 170–172° C.

Analysis: Calculated for $C_{21}H_{30}N_2.2HCl$: 72.70% C; 9.01% H; 8.08% N. Found: 72.79% C; 9.01% H; 7.76% N.

EXAMPLE 57

By following the manipulative procedure described above in Example 56(b), substituting ethylaminoethylamine for dimethylaminopropylamine, produces the corresponding compound of the invention. An oxalate salt is made and recrystallized from a methanol-water mixture to give 1-(2-ethylaminoethyl)-2-phenyl-4,5,6,7,8,9-hexahydrocyclooctu[b]pyrrole oxalate, dec. at 245° C.

Analysis: Calculated for $C_{20}H_{28}N_2.(CO_2H)_2$: 68.37% C; 7.82% H; 7.25% N. Found: 68.10% C; 7.92% H; 7.43% N.

EXAMPLE 58 a. A solution of 40.8 g (0.167 mole) of p-nitrophenacyl bromide in 125 ml. of dimethylformamide is added dropwise to a cooled solution of 30 g (0.167 mole) of 1-pyrrolidino-1-cyclooctene in 125 ml. of dry dimethylformamide. After stirring at ambient temperature for 24 hours, 500 ml. of water are added and the mixture is stirred for 3 hours. The reaction mixture is poured into 1500 ml. of water, and extracted with chloroform. The chloroform solution is washed with water, dried, and evaporated to a red oil which solidifies upon cooling to an orange solid, m.p. 94°–97° of 2-(p-nitrophenacyl)cyclooctanone.

b. 6.1 g (0.06 mole) of dimethylaminopropylamine a-e added dropwise to a stirred solution of 18.0 g (0.06 mole) of 2-(p-nitrophenacyl)cyclooctanone in glacial acetic acid under nitrogen. After refluxing for 5 hours, ice and water are added, and the aqueous solution is washed with ether. The aqueous solution is basified with sodium carbonate solution and extracted with ether. The ether solution is washed with water, dried, and evaporated to a red oil. The oil solidifies upon cooling. The solid is converted to a hydrochloride salt which is recrystallized twice from an isopropanol-ether mixture to give 1-(3-dimethylaminopropyl)-2-(p-nitrophenyl)-4,5,6,7,8,9-hexahydrocyclooctu[b]-pyrrole hydrochloride, m.p. 203° C.

Analysis: Calculated for $C_{21}H_{29}N_3O_2.HCl$: 64.35% C; 7.72% H; 10.72% N. Found: 64.53% C; 7.87% H; 10.57% N.

EXAMPLE 59

9.0 g (0.025 mole) of 1-(3-dimethylaminopropyl)-2-(p-nitrophenyl-4,5,6,7,8,9-hexahydrocyclooctu[b]pyrrole (free base of Example 58), is treated according to the manipulative procedure described above in Example 53 to give 1-(3-dimethylaminopropyl)-2-(p-aminophenyl)-4,5,6,7,8,9-hexahydrocyclooctu[b]pyrrole dioxalate monohydrate, dec. at 155° C.

Analysis: Calculated for $C_{21}H_{31}N_3.2(CO_2H)_2.H_2O$: 57.34% C; 7.12% H; 8.03% N. Found: 57.02% C; 7.04% H; 7.73% N.

EXAMPLE 60 a. A solution of 24.1 g (0.11 mole) of p-fluorophenacylbromide in 100 ml. dimethylformamide is added dropwise to a cooled solution of 20 g (0.11 mole) of 1-pyrrolidino-1-cyclooctene in 125 ml. of dimethylformamide. After stirring at ambient temperature for 20 hours, 500 ml. of water are added and the mixture is stirred for 3 hours. The reaction mixture is then poured into 1500 ml. of water and extracted with chloroform. The chloroform solution is washed, dried, and evaporated, leaving a dark oil. The oil is stirred at 100° C. for 2 hours under a high vacuum. Upon cooling the oil solidifies to a tan solid, m.p. 55°–58°, of 2-(p-fluorophenacyl)cyclooctanone.

b. 2.7 g (0.027 mole) of dimethylaminopropylamine are added to a stirred solution of 7.0 g. (0.027 mole) of 2-(p-fluorophenacyl)cyclooctanone in absolute ethanol under nitrogen. A few drops of concentrated hydrochloric acid are added and the reaction mixture is refluxed for 6 hours. The reaction is poured into water, the pH is adjusted to 1, and the aqueous solution is washed with ether. The aqueous solution is basified with sodium carbonate solution and extracted with ether. The ether solution is washed with water, dried, and concentrated to a yellow oil. The oil is converted to an oxalate salt which is recrystallized twice from a methanol-ether mixture to give 1-(3-dimethylaminopropyl)-2-(p-fluorophenyl)-4,5,6,7,8,9-hexahydrocyclooctu[b]pyrrole oxalate, dec. at 209°–210° C.

Analysis: Calculated for $C_{21}H_{29}FN_2.(CO_2H)_2$: 66.00% C; 7.47% H; 6.70% N. Found: 65.52% C; 7.48% H; 6.69% N.

EXAMPLE 61 a. By following the manipulative procedure described in Example 60(a), substituting p-methoxyphenacylbromide for p-fluorophenacylbromide, gives 2-(p-methoxyphenacyl)-cyclooctanone, m.p. 54°–56° C. b. 5.1 g (0.05 mole) of dimethylaminopropylamine are added dropwise to a stirred solution of 13.7 g (0.05 mole) of 2-(p-methoxyphenacyl)cyclooctanone in glacial acetic acid. After refluxing for 5 hours, ice and water are added and the solution washed with ether. The aqueous solution is basified with sodium carbonate solution and extracted with ether. The ether solution is washed with water, dried, and concentrated to a brown oil. The oil is converted to an oxalate salt which is recrystallized 3 times from a methanolether mixture to give 1-(3-dimethylaminopropyl)-2-(p-methoxyphenyl)-4,5,6,7,8,9-hexahydroocta[b]pyrrole oxalate, dec. at 180° C.

Analysis: Calculated for $(_{22}H_{32}N_2O.(CO_2H)_2$: 66.95% C; 7.96% H; 6.51% N. Found: 66.18% C; 7.83% H; 6.40% N.

We claim:
1. A pyrrole of the formula

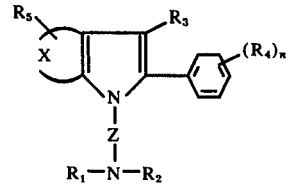

wherein Z is a straight or branched saturated hydrocarbon chain of from 2 to 5 carbon atoms; $R_1$ is hydrogen or alkyl of from 1 to 3 carbon atoms; $R_2$ is alkyl of from 1 to 3 carbon atoms or phenyl; $R_3$ is hydrogen, or phenyl; $R_4$ is alkyl of from 1 to 6 carbon atoms, alkoxy of from 1 to 4 carbon atoms, halogen, trifluoromethyl, hydroxy, nitro, cyano, amino, acetamido or phenyl; n is an integer from 0 to 3, inclusive; X is polymethylene of from 3 to 7 carbon atoms; and $R_5$ is hydrogen, alkyl of from 1 to 5 carbon atoms, alkoxy of from 1 to 2 carbon atoms or halogen; or a physiological tolerable acid addition salt thereof.

2. A compound as defined in claim 1 wherein Z is a straight or branched, saturated hydrocarbon chain of from 2 to 3 carbon atoms; $R_3$ is hydrogen or phenyl; $R_4$ is methyl, methoxy, bromo, chloro, fluoro, hydroxy, trifluoromethyl nitro, amino or cyano; X is polymethylene of from 3 to 6 carbon atoms; and $R_5$ is hydrogen, alkyl of from 1 to 4 carbon atoms or methoxy.

3. The compound defined in claim 2 which is 1-(3dimethylene)-2-phenyl-1,4,5,6,-tetrahydrocyclopenta[b]pyrrole and the physiologically tolerable acid addition salts thereof.

4. The compound defined in claim 2 which is 1-(3-dimethylaminopropyl)-2-(p-bromophenyl)-4,5,6,7-tetrahydroindole and the physiologically tolerable acid addition salts thereof.

5. The compound defined in claim 2 which is 1-(3-dimethylaminopropyl)-2-(p-methoxyphenyl)-4,5,6,7-tetrahydroindole and the physiologically tolerable acid addition salts thereof.

6. The compound defined in claim 2 which is 1-(2-methylaminoethyl)-2-(m-trifluoromethylphenyl)-4,5,6,7-tetrahydroindole and the physiologically tolerable acid addition salts thereof.

7. The compound defined in claim 2 which is 1-(3-dimethylaminopropyl)-2,3-diphenyl-4,5,6,7-tetrahydroindole and the physiologically tolerable acid addition salts thereof.

8. The compound defined in claim 2 which is 1-(2-methylaminoethyl)-2-phenyl-1,4,5,6,7,8-hexahydrocyclohepta[b]pyrrole and the physiologically tolerable acid addition salts thereof.

9. The compound defined in claim 2 which is 1-(3-)-2-phenyl-1,4,5,6,7,8-hexahydroxy clohepta[b]pyrrole and the physiologically tolerable acid addition salts thereof.

10. The compound defined in claim 2 which is 1-(3-diethylaminopropyl)-2phenyl-1,4,5,6,7,8-hexahydrocyclohepta[b]pyrrole and the physiologically tolerable acid addition salts thereof.

11. The compound defined in claim 2 which is 1-(1methyl-2dimethylaménoethyl)-2-phenyl-1,4,5,6,7,8-hexahydrocyclohepta[b]pyrrole and the physiologically tolerable acid addition salts thereof.

12. The compound defined in claim 2 which is 1-(3-methylaminopropyl)-2-(p-methoxyphenyl)-1,4,5,6,7,8-hexahydrocyclohepta[b]pyrrole and the physiologically tolerable acid addition salts thereof.

13. The compound defined in claim 2 which is 1-(2-ethylaminoethyl)-2-phenyl-4,5,6,7,8,9-hexahydrocycloocta[b]pyrrole and the physiologically tolerable acid addition salts thereof.

14. The compound defined in claim 2 which is 1-(3-dimethylaminopropyl)-2-(p-aminophenyl)-4,5,6,7,8,9-hexahydrocycloocta[b]pyrrole and the physiologically tolerable acid addition salts thereof.

* * * * *

UNITED STATES PATENT AND TRADEMARK OFFICE
CERTIFICATE OF CORRECTION

PATENT NO. : 3,997,557
DATED : December 14, 1976
INVENTOR(S) : Helsley et al.

It is certified that error appears in the above-identified patent and that said Letters Patent are hereby corrected as shown below:

In the Abstract, change

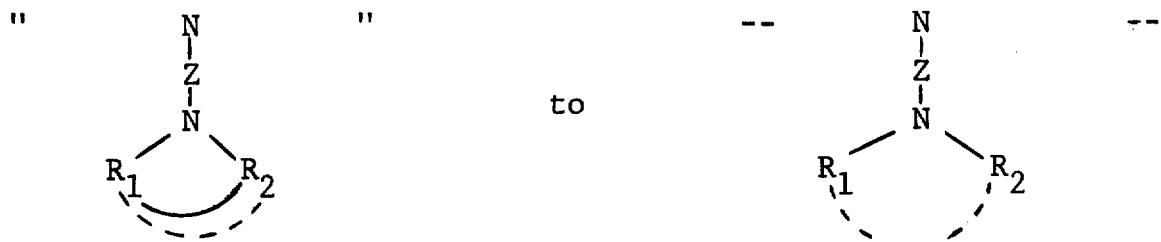

and

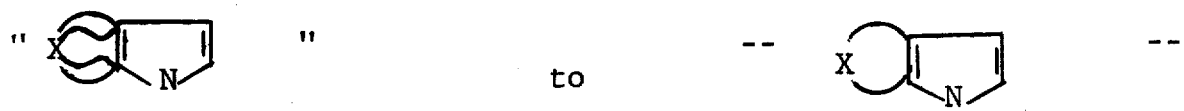

Columns 1 and 2, change

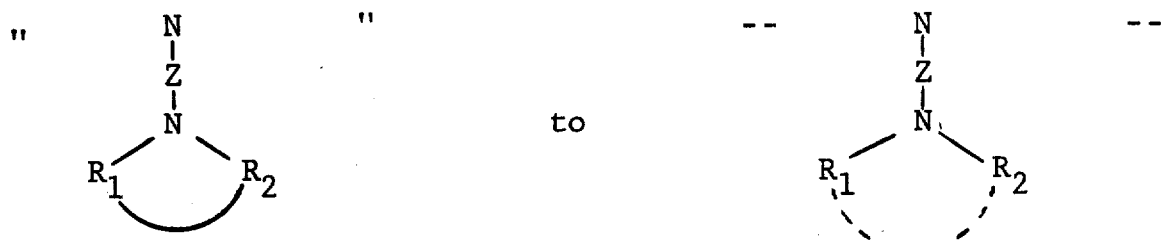

UNITED STATES PATENT OFFICE
CERTIFICATE OF CORRECTION

Patent No. 3,997,557                      Dated December 14, 1976

Inventor(s) Helsley et al.                Page 2 of 5

It is certified that error appears in the above-identified patent and that said Letters Patent are hereby corrected as shown below:

Column 3, line 6, change "...phenyl)4,..." to --...phenyl)-4,...--;

Column 4, Table II, in the ninth compound, after "...dimethylaminoethyl)-2" add a hyphen (-);

Column 5, line 30, change "...[e]-indole" to --...[e]indole--;

line 45, change "suspension" to --suspensions--;

Column 6, line 57, change "...phenyl4,5,6,7-..." to --...phenyl-4,5,6,7-...--;

Column 7, Table IV, under "Z," Example 2, change "(CH$_2$)$_2$" to --(CH$_2$)$_2$--;

Table IV, under "R$_1$NR$_2$," Example 5, change

" 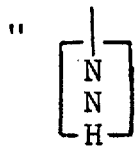 "   to   -- 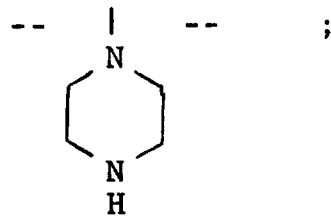 --  ;

line 43, change "...phenacyl)    cyclohexanone" to --...phenacyl)cyclohexanone--;

line 55, change "...-2(p-..." to --...-2-(p-...--;

UNITED STATES PATENT AND TRADEMARK OFFICE
CERTIFICATE OF CORRECTION

PATENT NO. : 3,997,557
DATED : December 14, 1976
INVENTOR(S) : Helsley et al.

It is certified that error appears in the above-identified patent and that said Letters Patent are hereby corrected as shown below:

Column 8, line 27, before "A suspension" insert --a.--;

Column 9, line 33, change "manipulation" to --manipulative--;

Column 10, line 55, change "...phenacyl)   cyclohexanone" to --...phenacyl)cyclohexanone--;

Column 13, line 8, change "6.01%H" to --6.01%N--;

line 9, change "6.31%H" to --6.31%N--;

line 16, change "G" to --g--;

line 54, change "Addition" to --addition--;

Column 14, line 34, change "dimethyl   amino..." to --dimethylamino...--;

line 35, change "...propyl)-    4,5-..." to --...propyl)-4,5-...--;

line 58, change "...[e]   indole" to --...[e]indole--;

Column 15, Table VI, in the heading, change the structure

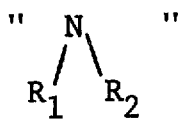   to   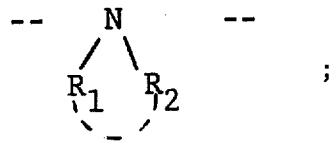   ;

UNITED STATES PATENT OFFICE
CERTIFICATE OF CORRECTION

Patent No. 3,997,557　　　　　　　　　Dated December 14, 1976

Inventor(s) Heisley et al

It is certified that error appears in the above-identified patent and that said Letters Patent are hereby corrected as shown below:

Column 17, line 9, before "By following" delete "a.";

line 66, change "...propyl)-minopropyl-2-..." to --...propyl)-2-...--;

Column 18, line 46, change "...phenyl)1,4,..." to --...phenyl)-1,4,...--;

line 66, change "...amino-propyl)-..." to --...aminopropyl)-...--;

Column 19, line 26, change "$C_{20}H_{27}N_3O \cdot _2HCl$" to --$C_{20}H_{27}N_3O_2 \cdot HCl$--;

line 32, before "the free base of" add --(--;

line 33, change "hydrogenerated" to --hydrogenated--;

line 45, change "$C_{20}H_{29}N \cdot _3 2(...$" to --$C_{20}H_{29}N_3 \cdot 2(...$--;

Column 20, line 11, change "32,6 g" to --32.6 g--;

Column 21, line 1, change "$C_{21}H_{30}N \cdot _2HCl$" to --$C_{21}H_{30}N_2 \cdot HCl$--;

line 32, change "a-e" to --are--;

Column 22, line 31, change "...phenacyl)-cyclo..." to --...phenacyl)cyclo...--;

line 31, "b. 51 g" should start a new paragraph;

line 41, change "methanolether" to --methanol-ether--;

line 44, change "$(_{22}H_{32}...$" should be --$C_{22}H_{32}...$--;

UNITED STATES PATENT AND TRADEMARK OFFICE
CERTIFICATE OF CORRECTION

PATENT NO. : 3,997,557
DATED : December 14, 1976
INVENTOR(S) : Helsley et al.

It is certified that error appears in the above-identified patent and that said Letters Patent are hereby corrected as shown below:

Claim 2, line 7, after "trifluoromethyl" add a comma (,);

Claim 3, line 11, change "(3dimethylene)-2-phenyl-..." to
--(3-dimethylaminopropyl)-2-phenyl-...--;

Claim 9, line 5, change "1-(3-)-2-phenyl..." to
--1-(3-diethylaminopropyl)-2-phenyl...--;

line 6, change "...hydroxy clohepta..." to
--...hydroxycyclohepta...--;

Claim 10, line 10, change "...-2phenyl..." to --...-2-phenyl...--;

Claim 11, line 14, change "(1methyl-2dimethylamenoethyl)..." to
--(1-methyl-2-dimethylaminoethyl)...--.

Signed and Sealed this

Third Day of May 1977

[SEAL]

Attest:

RUTH C. MASON
*Attesting Officer*

C. MARSHALL DANN
*Commissioner of Patents and Trademarks*